United States Patent [19]

Nishioka et al.

[11] 4,386,157

[45] May 31, 1983

[54] METHOD FOR DETECTING COLIFORM ORGANISMS

[76] Inventors: James M. Beggs, Administrator of the National Aeronautics and Space Administration, with respect to an invention of Kenji Nishioka, Redwood City; David A. Nibley, Mountain View, both of Calif.; Eldon L. Jeffers, La Porte, Tex.; Richard L. Brooks, Mountain View, Calif.

[21] Appl. No.: 315,278

[22] Filed: Oct. 26, 1981

[51] Int. Cl.³ .......................... C12Q 1/06; C12Q 3/00; C12Q 1/04; C12Q 1/10
[52] U.S. Cl. .......................................... 435/39; 435/3; 435/34; 435/38; 435/807
[58] Field of Search .................. 435/34, 39, 40, 3, 289, 435/291, 807, 38

[56] References Cited

U.S. PATENT DOCUMENTS

| | | | |
|---|---|---|---|
| 3,740,320 | 6/1973 | Arthur | 435/39 |
| 3,907,646 | 9/1975 | Wilkins et al. | 435/39 |
| 4,009,078 | 2/1977 | Wilkins et al. | 435/39 X |
| 4,030,979 | 6/1977 | Zuber | 435/39 |
| 4,204,037 | 5/1980 | Dill et al. | 435/291 X |
| 4,209,299 | 6/1980 | Carlson | 436/150 |
| 4,246,343 | 1/1981 | Wilkins et al. | 435/39 X |

*Primary Examiner*—Robert J. Warden
*Attorney, Agent, or Firm*—Darrell G. Brekke; John R. Manning

[57] ABSTRACT

A method and apparatus are disclosed for determining the concentration of coliform bacteria in a sample. The sample containing the coliform bacteria is cultured in a liquid growth medium. The cultured bacteria produce hydrogen and the hydrogen is vented to a second cell containing a buffer solution in which the hydrogen dissolves. By measuring the potential change in the buffer solution caused by the hydrogen, as a function of time, the initial concentration of bacteria in the sample is determined. Alternatively, the potential change in the buffer solution can be compared with the potential change in the liquid growth medium to verify that the potential change in the liquid growth medium is produced primarily by the hydrogen gas produced by the coliform bacteria.

6 Claims, 3 Drawing Figures

METHOD FOR DETECTING COLIFORM ORGANISMS

DESCRIPTION

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

TECHNICAL FIELD

The present invention generally relates to methods and apparatus for making quantitative determinations of bacteria present in water. More particularly, the invention relates to methods and apparatus for making quantitative determinations of coliform organisms present in water such as waste water, effluent or fresh water by using electrochemical techniques based only on detection of metabolic hydrogen liberated by coliform organisms utilizing changes in electrode potentials.

BACKGROUND ART

Detection in quantitative measurement of the number of coliform bacteria present in water is frequently of vital importance for determining the effectiveness of water treatment processes in removing bacterial contamination. The presence in sewage of coliform bacteria make this organism a sensitive indicator of pollution. Coliform, along with other bacteria, are also quite readily removed from water by conventional water purification processes. The common intestinal bacteria pathogens are at least as susceptible to the artificial and natural purification processes to which water is subjected as is the more common coliform bacteria. Therefore, the coliform group may be employed as a good indicator of bacterial pollution.

As discussed in U.S. Pat. No. 4,204,037 (Dill et al), there are presently several methods known for the detection of coliform bacteria in aqueous solutions. These methods are generally divided into two classes of detection, both being based on the production of metabolic hydrogen liberated by the coliform organisms after inoculation into a lactose broth. One such method, disclosed in U.S. Pat. No. 3,907,646 (Wilkins et al), measures the increase in pressure due to metabolically produced hydrogen where the coliform bacteria are cultured in a hermetically sealed chamber. Another method, disclosed in U.S. Pat. No. 4,009,078 (Wilkins et al) utilizes a test tube containing two electrodes positioned in the growth nutrient broth containing coliform organisms. Hydrogen evolution is measured by an increase in voltage in a negative direction caused by the metabolic hydrogen production. In U.S. Pat. No. 4,204,037, an automated apparatus and method for detecting coliform organisms by measuring the increase in voltage caused by metabolic hydrogen in the growth medium is disclosed.

An apparatus and method for measuring the amount of gas absorbed or released by a substance has also been disclosed in U.S. Pat. No. 3,740,320 (Arthur). In the system disclosed in this patent, the air from the top of the closed chamber containing the water solution is circulated through a gas analyzer. The changes in a particular gas caused by the bacterial activity in the sample solution are determined by the gas analyzer. From this information, the activity of the bacteria in the solution is determined.

It has also been disclosed in the prior art that the quantitative determination of a particular type of volatile material in a liquid can be determined by first transferring the desired volatile to a liquid of known conductivity. The change in conductivity of the liquid to which the volatile material has been transferred indicates the quantitative amount of the volatile contained in the sample. A method and apparatus of this type is disclosed in U.S. Pat. No. 4,209,299 (Carlson).

SUMMARY OF THE INVENTION

While the methods and techniques described above have been proven useful, it has been found that certain non-coliform organisms have an effect on the potential change measured by the electrodes in the liquid growth medium, and differentiation between coliform and certain non-coliform bacteria has not been provided for in the prior art. The present invention overcomes the problems associated with prior art techniques through the provision of a method and apparatus for determining the concentration of coliform bacteria contained in a aqueous sample in a liquid growth medium by the hydrogen produced by the coliform bacteria only, so that the effects of non-coliform bacteria are eliminated.

According to one preferred embodiment of the present invention, a sample containing the coliform bacteria is cultured in a liquid growth medium so that hydrogen is evolved by the coliform bacteria. This hydrogen gas is vented to a buffer solution in which the hydrogen dissolves. The electrical potential in the buffer solution is then measured. The time interval between the time of initiation of the culturing of the bacteria and the time that a pre-selected potential change is reached is used to determine the initial concentration of coliform bacteria in the sample. By venting the hydrogen gas to a separate buffer solution, errors attributable to non-coliform bacteria are obviated.

According to another embodiment of the present invention, a liquid sample containing coliform bacteria is introduced into a liquid growth medium contained in a first electrochemical cell. The change in electrical potential of the liquid growth medium is measured as hydrogen gas is evolved by the coliform bacteria. As the hydrogen is evolved by the coliform bacteria, the hydrogen is vented to a second electrochemical cell containing a buffer solution in which the hydrogen dissolves. The change in potential of the buffer solution is also measured. Comparison of the changes in potential of the liquid growth medium with the changes in potential of the buffer solution enables verification of the fact that the majority of the change in potential occurring in the liquid growth medium is caused by the evolution of hydrogen gas.

A completely automated electrochemical measuring apparatus and method can also be provided using the present invention. This system which is operated and controlled by a digital computer, provides that the coliform bacterial concentration of a sample body of water can be periodically and continuously monitored. The control apparatus provides for the culturing of the aqueous sample, measuring the potential difference produced by the metabolically induced hydrogen, discharging the sample, and cleaning and sterilizing the equipment in preparation for repeating the cycles.

Accordingly, it is an object of the present invention to provide a method and apparatus for quantitatively determining the concentration of coliform bacteria in an aqueous sample.

An important feature of the present invention is that the determination of coliform bacteria by the evolution of hydrogen is relatively unaffected by non-coliform bacteria.

Another object of the present invention is to provide an automated method and apparatus to determine quantitatively the concentration of both total coliform and fecal coliform bacteria contained within an aqueous solution.

Yet another object of the present invention is to provide an automated method and apparatus for quantitatively determining the concentration of coliform bacteria and for discharging the bacteria culture and cleaning and sterilizing the bacterial growth cell after each concentration measurement.

These and other objects and features of the present invention will become apparent from the following detailed description when considered in conjunction with the accompanying drawings.

IN THE DRAWINGS

DETAILED DESCRIPTION

As mentioned above, U.S. Pat. No. 4,204,037 (Dill et al) describes a method and apparatus for detecting coliform organisms by the hydrogen induced change of potential in a liquid growth medium contained in a cell. As will appear, the preferred embodiment of the invention is an improvement on the method and apparatus of the Dill et al patent and the contents of that patent are hereby incorporated by reference.

Figure 1:
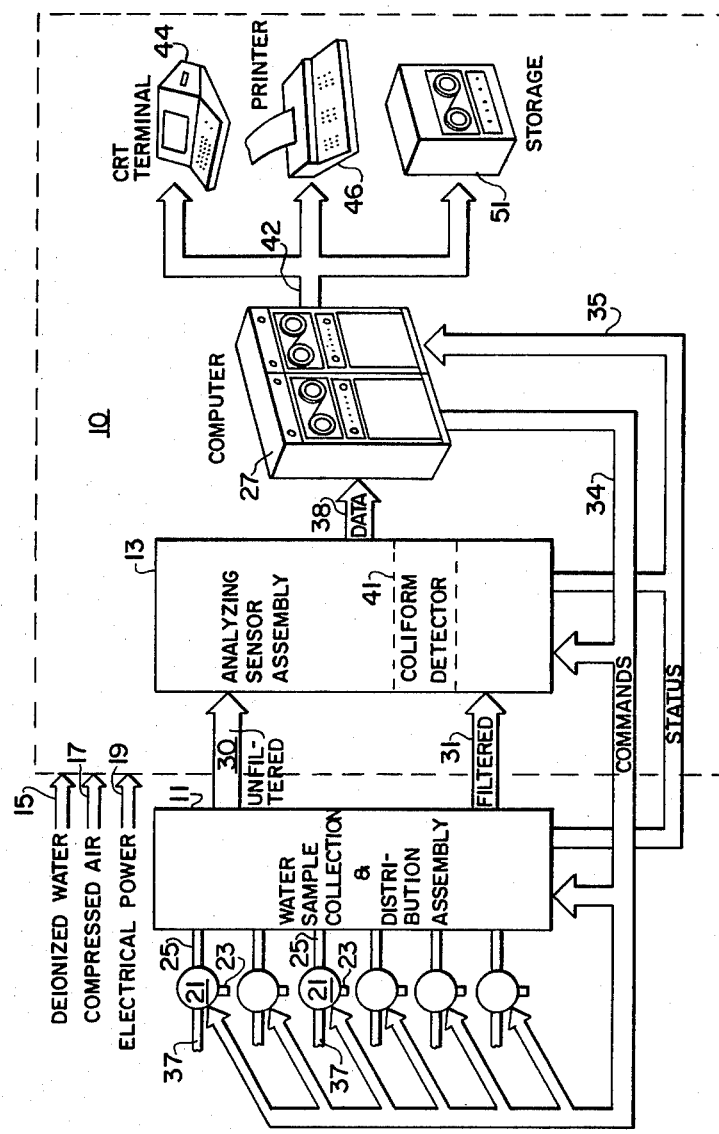
FIG. 1 is a pictorial/block diagrammatic representation disclosing the various assemblies making up a portable water monitoring system of which the present invention forms an important subassembly.

Referring now to FIG. 1, an automated water monitoring system 10 incorporating the present invention is shown. The water monitoring system 10 includes a input water sample collection and distribution assembly 11 interconnected to one or more remotely located water sampling locations. System 10 also includes an analyzing sensor assembly 13, which comprises various analyzing subassemblies useful in determining the chemistry of aqueous solutions, and in addition, the biological quality of the samples taken from the various remote sampling locations along the process flow path in a water treatment system.

Adjacent the analyzing sensor assembly 13, is located a digital computer 27 which provides process and sequencing control signals for automated testing of the water samples. Digital computer 27 receives the data signals from the various analyzers of assembly 13 after those signals have passed through an analog-to-digital converter which converts the signals to a form acceptable to computer 27. Use of the digital computer 27 allows the water monitoring system 10 to be completely automated, enabling operation of the system with a minimum of personnel.

Input connections 15, 17, and 19 are provided for deionized water, compressed air and electrical power, respectively, for use in system 10. Other consumables required for system 10 are analytical gases and chemical reagents. Of course, in remote locations or where the water, compressed air or electrical power is not available, suitable sources contained within system 10 may be provided.

Water monitoring system 10 is designed for mounting in a typical instrumentation trailer (not shown). When mounted in such a trailer, system 10 is readily transportable to any desired location for monitoring the quality of water at that location. Suitable locations, for example, could be a sewage treatment plant, industrial effluent discharge, or other locations where permanent water quality monitoring systems are not feasible or justified.

When water monitoring system 10 is positioned adjacent the desired facility, such as a waste water treatment plant (not shown), a plurality of sampling pumps (not shown) are positioned in the water treatment flow path in the plant to allow the collection of samples at various points along the flow path in the plant. These sampling points are connected via sampling lines 37 and valves 21 to sampling collection and distribution assembly 11. As described above, the sample collection points, including the sampling pumps, may be remote from sample collection and distribution assembly 11.

Sample collection valves 21 are energized in response to signals received from digital computer 27 over conductor 34. The sample collection and distribution assembly 11 is also controlled by commands from the digital computer 27 over conductor 34, the command interface line. Additionally, status signals representing the "on-off" condition of valves 21 are transmitted to the digital computer 27 over conductor 35, the status interface line.

When a valve 21 is energized, it will allow the sampling line 37 it controls to flow a water sample into sample collection and distribution assembly 11 through pipe or tubing 25. This flow of water sample is pumped from the plant flow stream through sampling line 37, valve 21 and pipes or tubing 25 into the sample collection and distribution assembly 11. Each valve 21 is a two-way valve. To prevent bacteria buildup in pipes 37, the sample is always flowing and is either routed to pipe 25 or effluent pipe 23. The sample may then be processed by a filter (not shown) internal to the sample collection and distribution assembly 11 in response to commands from digital computer 27. As hereinabove described, deionized water, compressed air, and electrical power may be supplied to system 10 through connections 15, 17, and 19, respectively.

Dependent upon the measurement desired, sample collection and distribution assembly 11 can provide the various analyzers and sensor assembly 13 with an unfiltered sample from valves 21 over conduit 30 or with a filtered sample from one of the valves 21 over conduit 31. Water samples brought into the analyzing sensor assembly 13 over conduits 30, 31 are routed through various water chemistry and biological detection devices. Analyzing sensor assembly 13 includes a coliform detector subassembly 41. Additionally, assembly 13 may include apparatus for measuring the following water quality parameters: Total biomass, TOC (total organic carbon), turbidity, DO (dissolved oxygen), ph, ammonia, chloride, nitrate/nitrite, electrical conductivity, temperature, halocarbons, sodium, residual chlorine and hardness. The coliform detector subassembly 41 which forms the subject matter of the present invention will be hereinafter further described in greater detail.

As the various analyzers contained within analyzing sensor assembly 13 perform their various functions, the data is collected and transmitted to digital computer 27 via sensor/computer data interface 38. The processed digital data may be transmitted over a cable 42 to parallel feed a cathode ray tube terminal 44, a printer 46, and a storage device 51 such as a disk or tape recorder.

Prior to describing in great detail the apparatus comprising the present invention, it may be helpful to describe in simpler terms the hydrogen detection process which the apparatus of the present invention utilizes. The detection technique herein utilized is based on the principle that coliform bacteria characteristically evolve hydrogen gas during the metabolism of the disaccharide lactose.

Figure 2:
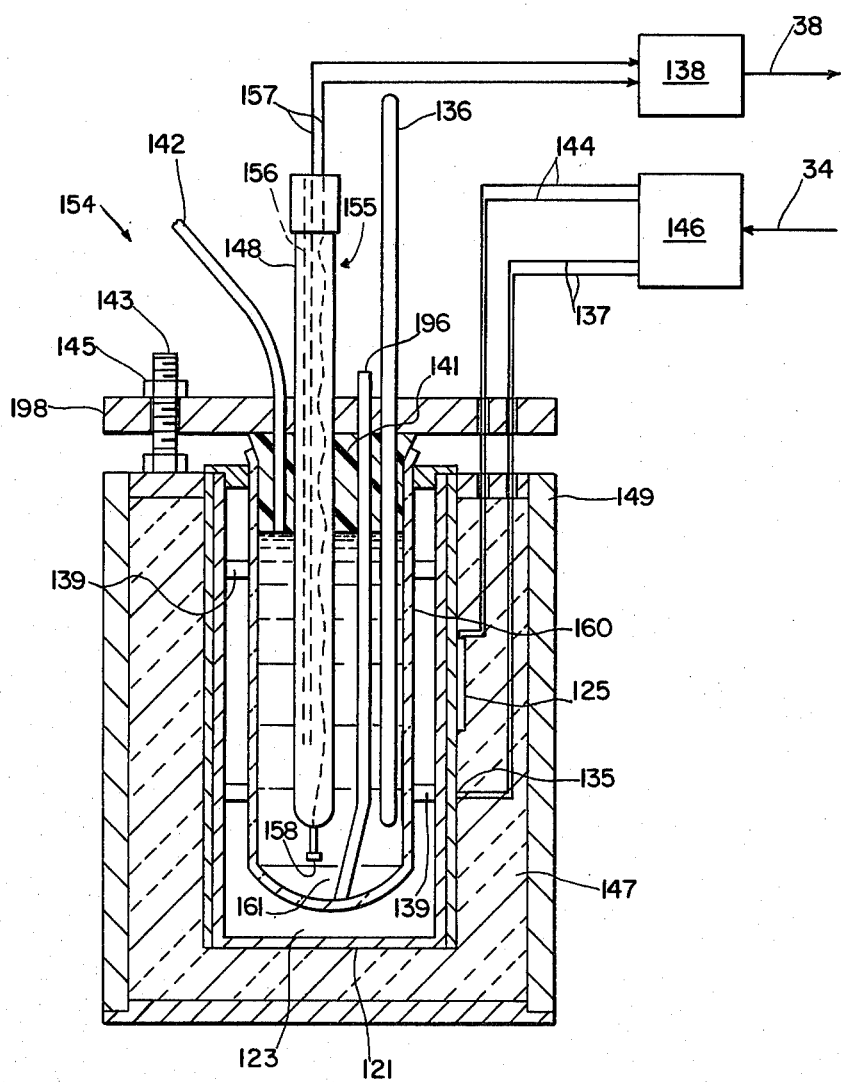
FIG. 2 is an exploded view of the electroanalytical cell and measuring electrodes forming the electrical potential measuring subassembly of this invention.

Referring now to FIG. 2, there is shown an electroanalytical cell 154 used in the embodiments herein described. Cell 154 includes a shell 121 which supports an oil bath 123. Shell 121 is wrapped along the sides and the lower end with a conventional insulating material 147. The insulated shell is then positioned in an open ended casing 149.

A holding cell 160, preferably a glass test tube, is positioned in oil bath 123 and a pliable stopper 141 is inserted into the open end of holding cell 160 and held in place by a retainer plate 198. Plate 198 is in turn held in place by the use of threaded rods 143 and mating nuts 145 as shown in detail in FIG. 2. To prevent damage to the glass envelope of holding cell 160, a plurality of spacers 139 are provided and positioned between the exterior of cell 160 and the interior of shell 121 to hold the glass envelope in spaced-apart relation to shell 121 within oil bath 123.

A conventional resistance heater 125 is bonded to the exterior of shell 121. A pair of electrical leads 144 connect the heater to temperature controller 146. Controller 146 utilizes a feedback circuit including a thermistor transducer 135 which is secured to shell 121 and electrically coupled to controller 146 via conductors 137. The thermistor responds to the actual temperature of shell 121 and controls the electric power supplied to heater 125 so that the temperature of shell 121 is maintained at a desired setting.

In accordance with the subject invention, it is necessary to measure the oxidation-reduction potential of liquid 161 in reservoir 160. In order to measure the potential of any electrode, it is necessary, in principle, to combine the electrode with a reference electrode having a known potential. Herein, a combination electrode 155 of the type commonly used for ph measurements is interposed through stopper 141 and retainer plate 198. The combination electrode includes a calomel reference electrode 156 enclosed within an electrically insulated jacket 148 and an end-mounted platinum electrode 158 that is wetted by liquid 161. The calomel reference electrode 156 and platinum electrode 158 are coupled to a high-impedance input signal conditioner 138 by conductors 157. The emf across the two half-cells and on electrodes 156 and 158 is a function of the potential of liquid 161. Combination electrode 155 may be, for example, electrode Model No. S-30101-15 manufactured by the Sargent-Welch Scientific Company.

A thermometer 136 penetrates plate 198 and stopper 141 and allows the temperature of liquid 161 to be externally monitored. Additionally, a tubing 196 extends through plate 198 to communicate with the lower portion of the interior of cell 160 for admitting and removing nutrient material, bacteria, cleaning and sterilizing agents or for admitting gas to liquid 161 contained therein. In addition, the cell is vented through a vent tube 142 interposed through stopper 141 and plate 198 to position the extremity flush with the bottom of stopper 141.

When the above-mentioned components, electrodes and thermometer have been positioned through the plate 198, each passage is sealed. Afterwards, the plate 198 is tightened against stopper 141 forcing the stopper into sealing engagement with the upper extremity of cell 160 to prevent a direct communication between oil bath 123 and the interior of cell 160.

Figure 3:
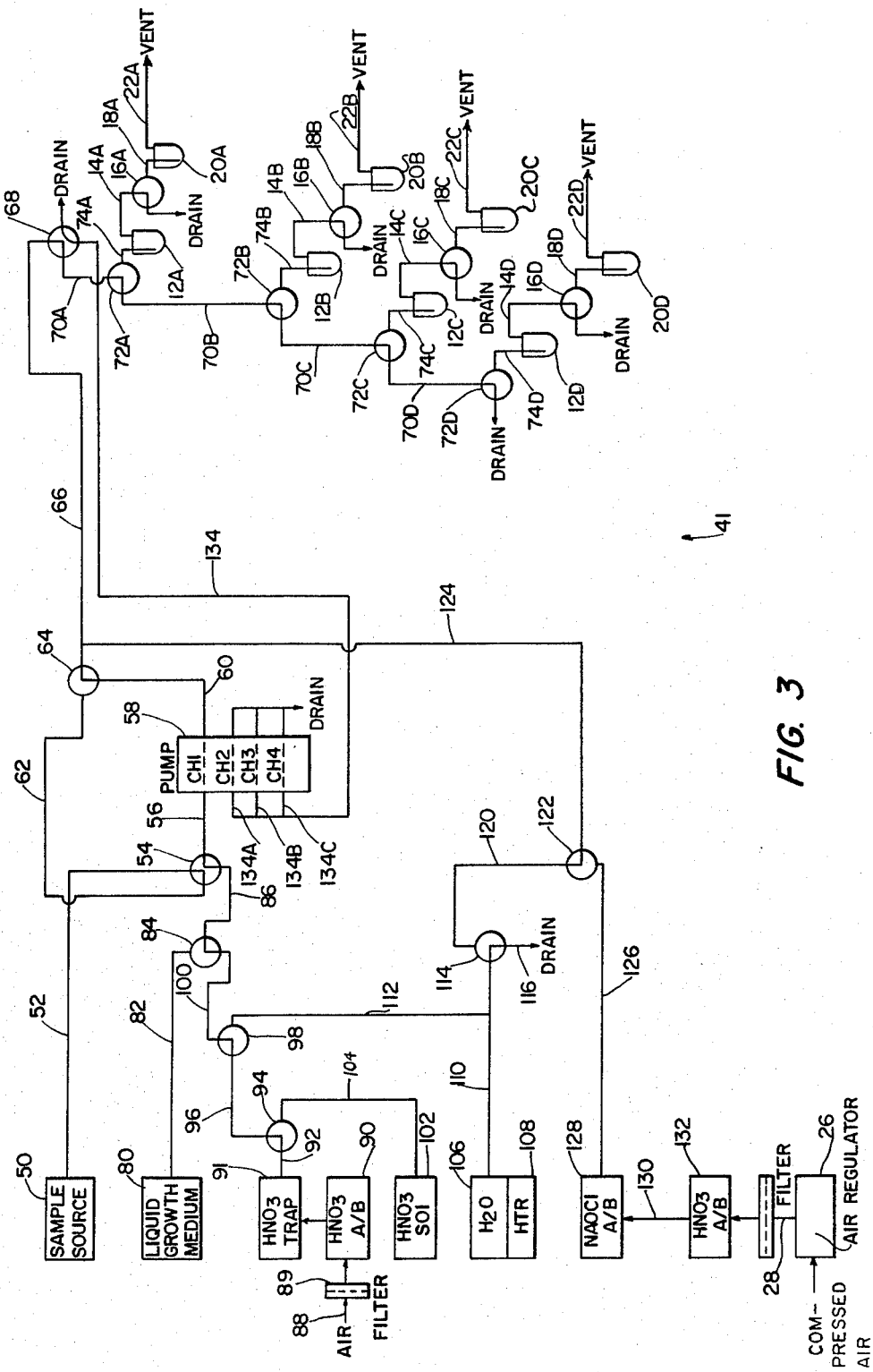
FIG. 3 is a simplified block diagram illustrating the automated apparatus for performing the coliform bacteria detection measurement of water samples in accordance with the method and apparatus of the present invention.

Referring now to the FIG. 3, an automated apparatus 41 for performing coliform detection measurements in accordance with the present invention is shown. This apparatus includes four electoanalytical culturing cells 12A, 12B, 12C, and 12D, collectively referred to as cells 12 which are the same as cell 154. In culturing cells 12, liquid 161 is a suitable liquid growth medium such as autoclaved double strength lauryl tryptose broth (DSLTB). Tube 142 of cell 12A is fluidly connected by a flexible tube 14A to a solenoid operated pilot valve 16A. One outlet of valve 16A is connected by a flexible delivery tube 18A to the tube (196) leading to the bottom of an electroanalytical hydrogen collecting cell 20A and the other outlet is connected to a drain. The tube (142) at the top of the collecting cell 20A is connected by a flexible outlet tube 22A to a vent. Similarly, culturing cells 12B, 12C, and 12D are connected to cells 20B, 20C and 20D, respectively. Collecting cells 20A, 20B, 20C and 20D, are referred to collectively as cells 20 and are the same as cell 154. In collecting cells 20, liquid 161 is a buffer solution in which hydrogen dissolves. A suitable buffer solution is a 1.0% potassium phosphate buffer solution and a suitable volume is 28 ml.

The automated apparatus also includes a sample source reservoir 50 from which the aqueous sample containing the coliform bacteria to be measured is obtained. Sample source 50 is connected by flexible tubing 52 to a solenoid operated pilot valve 54. A flexible tubing 56 connects one outlet of valve 54 to pump 58 and a flexible tubing 60 connects pump 58 to valve 64. One outlet of solenoid valve 64 is connected to a flexible tubing 66 which leads to a solenoid operated pilot valve 68. Sample fluid flowing in flexible tubing 66, and out of pilot valve 68, can be conducted to one of the culturing cells 12 after passing through one or more of flexible tubings 70A, 70B, 70C and 70D, solenoid operated pilot valves 72A, 72B, 72C and 72D, and flexible tubings 74A, 74B, 74C and 74D, as shown. An outlet of solenoid operated valve 72D is connected to a drain, as shown. By following the paths described above, a sample of fluid can bypass or be delivered to one or more of cells 12.

A liquid growth medium for use in culturing cells 12 is contained in a reservoir 80. Liquid growth medium reservoir 80 is connected by flexible tubing 82 to a solenoid operated pilot valve 84. The outlet of solenoid valve 84 is connected by flexible tubing 86 to solenoid valve 54. From solenoid valve 54, the liquid growth medium is conducted through flexible tubing 56 to pump 58, and from pump 58 conducted via flexible tubing 60 to solenoid valve 64. From solenoid valve 64 the medium can be transferred to culturing cells 12 as described above.

A source of air is connected by a tube 88 through a 0.45 micron filter 89, a nitric acid (HNO$_3$) air bath 90, and an acid trap 91 into flexible tubing 92. Flexible tubing 92 leads into a solenoid operated pilot valve 94 which in turn is connected by a flexible tubing 96 to a solenoid operated pilot valve 98. Solenoid valve 98 is then connected to an inlet of solenoid valve 84 by a flexible tubing 100. A nitric acid reservoir 102 is also connected to an inlet of solenoid valve 94 by flexible tubing 104.

A deionized water reservoir 106 is provided with an external heater and temperature controller 108 to elevate the temperature of the water to 95° C. Water reservoir 106 is connected by flexible tubing 110 and flexible tubing 112 to solenoid valve 98. Flexible tubing 110 also connects water reservoir 106 to a solenoid operated pilot valve 114. One outlet of solenoid valve 114 is connected by a flexible tubing 120 to a solenoid operated pilot valve 122. As shown, solenoid valve 122 is connected by a flexible tubing 124 to flexible tubing 66. The other inlet of solenoid valve 122 is connected by a flexible tubing 126 to a sodium hypochlorite (NaOCl) air bath 128. Sodium hypochlorite air bath 128 in turn is connected by a flexible tubing 130 to a second nitric acid air bath 132. As shown, flexible tubing 28 is connected through a 0.45 micron filter which is connected to air regulator 26 and is also connected to the second nitric air bath 132.

It should also be noted that one opening of solenoid valve 68 is connected to pump 58 by a flexible tubing 134. Flexible tubing 134 is split into three branches, 134A, 134B, and 134C. Branches 134A, 134B and 134C are all connected through pump 58 to a drain as shown.

It should be appreciated that this automated apparatus illustrated is operated by suitable means such as a digital computer (FIG. 1) which provides process and sequence control signals for automated testing of water samples. The various solenoid valves of the automated apparatus are controlled and operated by the digital computer. The various solenoid valves depicted in the figure are shown in their unenergized state.

Prior to describing in more detail the specific apparatus employed in the preferred embodiment of the present invention it may be helpful to describe in general terms the hydrogen detection process utilized by the apparatus of the present invention. The detection technique herein utilized is based on the principle that coliform bacteria characteristically evolves hydrogen gas during the metabolism of the liquid growth medium. Reference is again made to the Dill et al patent mentioned above which includes a lengthy discussion of the relationship between the hydrogen gas evolved by the coliform bacteria and the elapsed time period required for a particular potential change to occur in the liquid growth medium in which the coliform bacteria is cultured. However, as mentioned above, certain non-coliform bacteria may effect the potential measurement. For this reason, as the hydrogen is evolved in the culturing cell, the hydrogen is vented to the collecting cell. A measurement of (i) the potential change of the buffered solution contained in the collecting cell due to the introduction of the hydrogen verifies the presence of coliform bacteria in the culturing cells and (ii) the elapsed time period required for a predetermined millivolt change after introduction of the coliform bacteria into the culturing cell, provides a direct indication of the quantitative concentration of coliform bacteria contained in the original sample. It should be noted that because the potential change occurring in the buffer solution is caused solely by the evolved hydrogen, non-coliform bacteria which do not produce hydrogen do not effect this measurement. Thus, a measurement of the change in potential of the liquid growth medium in the culturing cell can be verified by comparing the measurement with the change in potential of the buffer solution.

It should also be appreciated that determination of the concentration of coliform bacteria can be provided solely by measuring the change in potential in the buffer solution together with the elapsed time period. Where the measurement of potential change in the buffer solution is used to determine initial coliform bacteria concentration, there is no need to measure the change in potential of the culturing medium since the change in potential of the buffer solution is caused solely by the hydrogen generated by the coliform bacteria. However, where measurements from both the liquid growth medium and the buffer solution are obtained, the two measurements act as a check on one another. The reason for this is that the non-coliform bacteria that effect the measurement in the liquid growth medium will not effect the buffer cell measurement. Thus, when no potential change is detected in the liquid growth medium but a significant change in potential occurs in the buffer solution this serves as an indication that a malfunction has probably occurred in the measuring system. Inasmuch as it is a potential change ($\Delta V$) that is measured, the precise voltage at the onset of a test is not significant.

Once a collection cell 20 is cleaned and sterilized and the buffer solution is introduced therein, the buffer solution may remain for innumerable tests. Unlike cells 12, cells 20 need not be purged of solution 161 after each test.

The operation of automated apparatus 41 will be described with reference to measurements made from culturing cell 12B and collecting cell 20B. However, it should be understood that the operation of the various pairs of culturing cells and collecting cells is similar except for the specific solenoid valves involved.

In operation, the interior of electroanalytical culturing cell 12B must first be cleaned and sterilized prior to culturing the liquid growth medium used in the detection process. The initial step of the clean up begins with draining spent nutrient from culturing cell 12B. This is accomplished by energizing solenoid valves 68, 72B and energizing channels 2, 3, and 4 of pump 58 for drawing spent nutrient from the interior of culturing cell 12B, through tubing 74B, valve 72B, tubing 70B, valve 72A, tubing 70A, valve 68, tubing 134, branches 134A, 134B, and 134C, through channels 2 and 3 and 4 of pump 58, and to the drain.

At the same time that culturing cell 12 is drained, solenoid valves 94 and 64 are actuated so that nitric acid is pumped from nitric acid reservoir 102, through tube 104, solenoid valve 94, tube 96, valve 98, tube 100, valve 84, tube 86, valve 54, channel 1 of pump 58, tube 60, valve 64, tube 62, valve 54, tube 52, and into sample reservoir 50. This effects bacteriostat of any organism which might be present and contaminate the sample as it is introduced into the culturing cells.

Next, channels 2, 3, and 4 of pump 58 and valves 64 and 68 are de-energized. Channel 1 of pump 58 and solenoid valve 94 are still energized so as to fill culturing cell 12B with nitric acid from reservoir 102. After de-energization of solenoid valve 94, solenoid valve 122 is energized to introduce an acid-treated, sodium hypochlorite (NaOCl) air wash from air regulator 26 (through acid air bath 132 and NaOCl air bath 128) into the interior of culturing cell 12B, causing the nitric acid within culturing cell 12B to be sprayed against the inner cell surface areas to effect bacteriostat of any organisms present within culturing cell 12B. After de-energization of solenoid valve 122, pump channels 2, 3, and 4, and valve 68 are energized to drain the nitric acid from within culturing cell 12B as mentioned above with respect to the draining of the spent liquid growth medium.

With all valves again de-energized as shown, ambient air from source 88 passes through filter 89, nitric acid air bath 90, and HNO$_3$ trap 91, where pump 58 draws the acid washed air from bath 90 through HNO$_3$ trap 91 and tubing 92, valve 94, tubing 96, valve 98, tubing 100, valve 84, tubing 86, valve 54, and tubing 56. From pump 58, the air is thereafter pumped through tubing 60, valve 64, tubing 66, valve 68, tubing 70A, valve 72A, tubing 70B, valve 72B, tubing 70C, valve 72C, tubing 70D, and valve 72D, to the system drain. Subsequently, deionized water received in water reservoir 106 is heated to 95° C. by heater 108 and thereafter drawn from reservoir 106 through tubing 110, tubing 112, energized valve 98, and along the same path followed by the acid washed air to the system drain at valve 72D to sterilize and clean the lines leading to culturing cells 12 including culturing cell 12B.

Pump channel 1 of pump 58 and solenoid operated valve 72B are then energized to fill the interior of culturing cell 12B with deionized water from water source 106 at an elevated temperature through valves 98, 84, 54, 64, 68, 72A and 72B. Upon completion of the deionized water fill of culturing cell 12B, pump channel 1 and valves 98 and 72B are de-energized. The process control means for the apparatus then signals the temperature controller for culturing cell 12B to elevate the temperature of the oil bath located in culturing cell 12B to maintain the temperature of the water in the cell at 85° C. This temperature of 85° C. is maintained for a one-half hour soak period. During this soak period, regulated air is forced into the cell as previously described to agitate the heated deionized water. Following the elevated temperature soak, valves 72B and 68 and pump channels 2, 3 and 4 are energized to drain the water from the interior of culturing cell 12B in the manner described above, after which valves 94, 72B and 68 and pump channels 2, 3 and 4 are deenergized.

After the hot water has been drained and while culturing cell 12B is empty, solenoid valves 16B, 72B and 122 are energized. Thus, regulated air is forced through culturing cell 12B and into collecting cell 20B to the vent. This is done to purge any hydrogen collected in the buffer solution in the collecting cell from the previous measurement. After purging, valve 122 and 16B are de-energized.

Next, pump channel 1 and valve 84 are energized to fill culture cell 12B with a predetermined volume of DSLTB or other suitable bacteria growth medium from liquid growth medium reservoir 80. Pump channel 1 and valves 84, and 72B are then de-energized and the temperature of the nutrient within cell 12B is elevated to 85° C. by operation of the temperature controller and heater mentioned above. Again, the temperature of the liquid growth medium is maintained at 85° C. for approximately one-half hour after which the process controller provides a stable temperature at either 35° C. or 44° C., dependent upon the type of coliform bacteria to be measured. Once the temperature is stabilized at the preselected temperature, pump channel 1 and solenoid operated valves 54 and 72B are energized briefly to permit inoculation of a sample from sample source 50. Pump channel 1 and valves 54 and 72B are then de-energized.

Metabolism by the coliform bacteria contained in the sample used to inoculate the culturing cell 12B produces molecular hydrogen during incubation from the lactose sugar contained in the DSLTB. As the number of bacteria increases and the molecular hydrogen concentration evolved from metabolism increases, the hydrogen is vented to collecting cell 20B where it is dissolved in the buffer solution. The evolving hydrogen causes an electrical potential change to occur in both the liquid growth medium in culturing cell 12B and the buffer solution contained in collecting cell 20B. This potential change is readily measured by the measuring and reference electrode pair, electrode 155, located in each cell. As discussed above, the potential change occurring in collecting cell 20B can be used to determine the initial concentration of bacteria in the fluid sample, or the potential change in collecting cell 20B can be used as a check to verify that the potential change measured in culturing cell 12B occurs primarily from the hydrogen produced there.

After a predetermined potential change, e.g., 200 mv. has occurred, or after a specific time period, e.g., 14 hours, has elapsed, the cycle is repeated for culturing cell 12B and collecting cell 20B. In a similar manner, all of the pairs of culturing cells 12 and collecting cells 20 can be appropriately cycled to provide additional measurements of the coliform bacteria concentration contained in the fluid samples from sample source 50. Preferably, in order to conserve the various fluids used, each step in the cycle is performed sequentially on all cells 12 and 20. This sequential operation is easily controlled by the process controller. It should also be appreciated that some cells 12 and 20 may be used to detect total coliform bacteria concentration while at the same time other cells 12 and 20 are used to detect fecal coliform bacteria concentration.

It will be obvious to one skilled in the art that the number of pairs of cells 12 and 20 can readily be altered to provide more or less pairs of cells 12 and 20. In addition, different and more effective solutions may be found for use in culturing cells 12 or collecting cells 20. Thus, while the invention has been described in detail with respect to an exemplary embodiment thereof, it will be understood by those of ordinary skill in the art that these and other variations and modifications may be effected in the exemplary embodiment within the scope and spirit of the invention.

What is claimed is:

1. A method of determining the concentration of a hydrogen producing bacteria contained in a sample comprising the steps of:

introducing the sample into a liquid growth medium contained in a first cell;

culturing the bacteria contained in the sample by maintaining the temperature at a preselected value such that metabolically produced hydrogen is evolved by the growth of the bacteria;

venting the evolved hydrogen into a buffer solution maintained at a predetermined temperature and contained in a second cell so that the hydrogen is dissolved in the buffer solution;

detecting a change in potential between a measuring electrode and a reference electrode in contact with the buffer solution resulting from the dissolved hydrogen;

measuring the time period between the introduction of the sample into the first cell and the detecting of a change in potential; and determining the concentration of the bacteria in the sample based on said detecting and measuring steps.

2. A method as claimed in claim 1 wherein the step of measuring the time period is performed when a predetermined change of potential is detected.

3. A method as claimed in claim 1 wherein the step of detecting of a change in potential is performed when a predetermined time period is measured.

4. A method of determining the concentration of bacteria as claimed in claim 1 wherein a new sample is periodically obtained from a fluid, introduced into a new liquid growth medium and measured, said method further comprising the steps of:

controlling the environment of the new liquid growth medium by maintaining the temperature of the growth medium at a temperature of approximately 85° C. for a heat-soak time period of approximately 30 minutes and cooling to 35° or 44° C. prior to the introducing of the new fluid sample; and discharging the liquid growth medium containing the cultured bacteria subsequent to the measuring and determining steps, initiating a cleaning and sterilizing cycle for removing bacterial residue remaining after discharge, removing the evolved hydrogen from the buffer solution subsequent to the measuring and determining steps, and repeating the steps recited above beginning with introducing the sample.

5. A method of determining the concentration of a hydrogen producing bacteria contained in a sample comprising the steps of:

introducing the sample into a liquid growth medium contained in a first cell;

culturing the bacteria contained in the sample by maintaining the temperature at a preselected value such that metabolically produced hydrogen is evolved by the growth of the bacteria;

detecting a first change in potential between a measuring electrode and a reference electrode in contact with the growth medium resulting from the evolved hydrogen;

generating a first electrical signal representative of the first change in potential;

measuring the period of time between the introduction of the sample and the detecting of a first change in potential;

venting the evolved hydrogen into a buffer solution maintained at a predetermined temperature and contained in a second cell whereby the hydrogen is dissolved in the buffer solution;

detecting a second change in potential between a measuring electrode and a reference electrode in contact with the buffer solution resulting from the dissolved hydrogen;

generating a second electrical signal representative of the second change in potential;

comparing the first signal generated from the growth medium with the second signal generated from the buffer solution to verify that the change in potential in the growth medium was caused by the evolving hydrogen; and determining the concentration of the bacteria in the sample fluid as a function of the measured period of time when the signal from the growth medium is verified.

6. A method of determining the concentration of bacteria as claimed in claim 5 wherein a new sample is periodically obtained from a fluid, introduced into a new liquid growth medium, and measured, comprising the further steps of:

controlling the environment of the new liquid growth medium by maintaining the temperature of the growth medium at a temperature of approximately 85° C. for a heat-soak time period of approximately 30 minutes and cooling to 35° or 44° C. prior to the introducing of the new fluid sample; and discharging the liquid growth medium containing the cultured bacteria subsequent to the measuring and determining steps, initiating a cleaning and sterilizing cycle for removing bacterial residue remaining after discharge, removing the evolved hydrogen from the buffer solution subsequent to the measuring and determining steps, and reinitiating the above steps beginning with introducing the sample.

* * * * *